(12) United States Patent
Cote et al.

(10) Patent No.: US 6,171,324 B1
(45) Date of Patent: Jan. 9, 2001

(54) MARKER FOR CORNEAL INCISION

(75) Inventors: Dana Michael Cote, Lynn; Joseph Francis Keenan, Cohasset; Michael Joseph Murphy, Norwood; Edwin G. Lee, Burlington, all of MA (US)

(73) Assignee: Becton, Dickinson and Company, Franklin Lakes, NJ (US)

( * ) Notice: Under 35 U.S.C. 154(b), the term of this patent shall be extended for 0 days.

(21) Appl. No.: 09/163,961

(22) Filed: Sep. 30, 1998

(51) Int. Cl.[7] ....................................................... A61F 9/00
(52) U.S. Cl. ............................................. 606/166; 606/167
(58) Field of Search ................................... 606/166, 167, 606/148; 351/212

(56) References Cited

U.S. PATENT DOCUMENTS

| | | | |
|---|---|---|---|
| 4,875,767 | * | 11/1989 | Wright .................................. 351/212 |
| 5,090,425 | * | 2/1992 | Stahl .................................... 606/148 |
| 5,569,280 | * | 10/1996 | Kamerling ............................ 606/166 |
| 5,578,049 | * | 11/1996 | Feaster ................................. 606/166 |
| 5,618,292 | * | 4/1997 | Poler .................................... 606/166 |
| 5,697,945 | * | 12/1997 | Kritzinger et al. ................... 606/166 |

OTHER PUBLICATIONS

Strength of Clear Corneal Incisions in Cadaver Eyes, Richard J. Mackool, M.D.; R. Scott Russell, M.D. J. Cataract Refract Surg—vol. 22, Jul./Aug. 1996 p. 721–725.*
Architecture and Construction of a Self–Sealing Incision for Cataract Surgery, I. Howard Fine, M.D. J. Cataract Refract Surg—vol. 17, Supplement 1991 p. 672–676.*

* cited by examiner

*Primary Examiner*—Michael Buiz
*Assistant Examiner*—Jonathan D. Goldberg
(74) *Attorney, Agent, or Firm*—John L. Voellmicke; Keith J. McWha (57) ABSTRACT

A corneal marker and a method of using a corneal marker are disclosed. The corneal marker includes a handle having a head coupled thereto. The inferior surface of the head includes a set of protuberances which form marking surfaces adapted to simultaneously engage corneal tissue. The marking surfaces form opposing sets of marks which allow a surgeon to form an incision of precise length and width. An alignment line on the superior and/or front surface of the marker facilitates the positioning thereof. A method of performing clear corneal surgery following the application of markings to the cornea is also provided.

18 Claims, 9 Drawing Sheets

MARKER FOR CORNEAL INCISION

BACKGROUND OF THE INVENTION

1. Field of the Invention

The field of the invention relates to medical marking devices for marking the eye prior to surgery, and a method of using a medical marking device to make a incision of a predetermined length and width.

2. Brief Description of the Prior Art

Medical marking devices have been developed for various surgical operations which involve making incisions in the eye. The marking devices are used prior to surgery, and provide markings to assist the surgeons in correctly locating the areas of the eye on which a keratome or other surgical knife is to be employed. Such devices function by leaving depressions in the eye or sets of ink marks. In either case, the markings identify the locations where incisions are to be made and/or sutures are to be placed.

Cataract extraction and lens implantation surgery is a commonly employed procedure. The techniques for performing such surgery have evolved over the years to the point where suturing the wound is often unnecessary. One procedure for conducting cataract surgery involves making an incision through both scleral and corneal tissue. Such a procedure for constructing a self-sealing incision during cataract surgery is described in the literature.[1] This procedure involves the use of a marker to create a grid of dots following cautery to allow selection of incision length and location. A perpendicular scleral groove is formed at the appropriate dots, followed by dissection of a scleral tunnel into clear cornea. The incision is complete when the selected keratome enters the anterior chamber. A more recent technique, called the clear corneal approach, is said to offer significant advantages over the above-described scleral approach. Whereas the scleral approach involves an incision through both scleral and corneal tissue, the primary incision is made substantially only through corneal tissue using the clear corneal approach. (The primary incision is used to remove the cataractous lens tissue and insert an intraocular lens.) Also, topical anesthesia may be used when employing the clear coneal approach.

Advantages of the clear corneal approach include faster patient visual recovery, the use of topical anesthesia, no subconjunctival hemorrhage, no cautery, and better refractive results. Selective location of the primary incision has also been said to allow correction for preoperative against-the-rule astigmatism.

The formation of a leak-proof, sutureless incision is desirable whether the scleral or clear corneal approach is employed. The risk of infection is believed to be significantly reduced if leakage can be avoided.

A corneal incision consists essentially of a tunnel created by a scalpel. The tunnel is composed of a "roof" and a "base". A corneal flap is formed at the distal end of the tunnel base. It is this flap that is pressed against the tunnel roof by intraocular pressure that actually seals the incision. A number of ophthalmologists have conducted research in developing the appropriate corneal incision architecture that would provide a reliable, leak-proof seal. The results of this research indicate that the tunnel length (i.e., the distance from the initial entry site to the tip of the corneal flap) is an important factor in determining the sealability of the incision.[2] A specific recommendation made by surgeons who have employed the clear corneal approach is to create an incision that has a maximum width to length ratio of about three to two.

SUMMARY OF THE INVENTION

The present invention is directed to a corneal marker which allows the length and width of an incision to be controlled within predefined limits. A method of making an incision in eye tissue of selected length and width is also provided.

In accordance with the invention, a corneal marker is provided which includes a handle and a head coupled to the handle. The head includes first, second, third, and fourth marking surfaces positioned for substantial simultaneous engagement of a human cornea. The first marking surface includes an elongate edge portion and is in opposed relation to the fourth marking surface. The second and third marking surfaces include elongate edge portions and are in opposed relation to each other along a second axis running perpendicular to the first axis. The marking surfaces define a generally rectangular outline wherein the width of the outline is about one and one-half times the length of the outline. The width of the outline is defined by the distance between the second and third marking surfaces and the length of the outline is defined by the distance between the first and fourth marking surfaces. The distance between the second and third marking surfaces is preferably but not limited to between about 2.0 and about 3.5 millimeters.

In further accordance with the invention, a corneal marker is provided which includes a handle, a head coupled to the handle, the head including a superior surface, an inferior surface, a front surface, and a rear surface. The rear surface is substantially arcuate to match the contour of the corneoscleral junction. First, second, third, and fourth protuberances extend from the inferior surface of the head. The protuberances include edge portions defining first, second, third, and fourth marking surfaces, respectively. The first protuberance adjoins the rear surface of the head and includes an arcuate edge portion defining the first marking surface. The fourth protuberance is in opposing relation to a central portion of the first protuberance along a first axis. The second and third protuberances are in opposing relation to each other along a second axis running perpendicular to the first axis. The distance between the second and third marking surfaces is between about 2.0 and about 3.5 millimeters. The distance between the first and fourth marking surfaces is less than the distance between the second and third marking surfaces. Preferably, the distance between the second and third marking surfaces is no more than fifty percent (50%) greater than the distance between the first and fourth marking surfaces.

A method is provided by the invention which includes the steps of marking the surface of an eye to provide first, second, third, and fourth markings thereon such that the first and fourth markings are in opposing relation along a first axis and the second and third markings are in opposing relation along a second axis running substantially perpendicular to the first axis. The distance between the second and third markings is not more than about fifty percent (50%) greater than the distance between the first and fourth markings. All four markings are made on corneal tissue. A groove is formed using a surgical knife along the first marking and between the second and third markings substantially perpendicularly into the eye tissue. A surgical knife is caused to form a tunnel running substantially parallel to the surface of the cornea beginning at the grooved end until the tip of the knife coincides with the fourth marking when viewed from the perspective of the surgeon. The knife handle is angled upward to cause the tip of the blade to angle downward, applanating the cornea. The blade is then moved forward into the anterior chamber to complete the incision.

DETAILED DESCRIPTION OF THE INVENTION

A corneal marker is disclosed, the preferred embodiment of which is shown in FIGS. 1–4. The marker 10 as shown in these figures includes a handle 12 and a head 14 coupled to the handle. While the head is permanently coupled or integral with the handle in accordance with the preferred embodiment, it will be understood that the two elements may be detachable to allow a plurality of different heads to be used with the same handle.

The head of the preferred marker is comprised of a generally trapezoidal block 16 having a superior surface 18, an inferior surface 20, a straight front surface 22, and an arcuate rear surface 24. The front surface 22 of head 14 corresponds with a fourth marking surface 40 for increased visibility of the cornea. The figures are greatly enlarged to show the structural details of these surfaces. The inferior surface extends at an oblique angle with respect to the longitudinal axis of the handle to facilitate its application to the cornea by a surgeon.

Referring to FIGS. 1–4, four protuberances extend from the inferior surface 20 of the block. Each of the protuberances is elongated and generally wedge-shaped in configuration. In a preferred embodiment of the invention, they extend about 0.5 mm from the inferior surface. The first protuberance 26 is arcuate and includes a rear wall which is angled 20° from the arcuate rear surface 24 of the block 16 to enhance visibility by the user intraoperatively. It further includes an arcuate edge defining a first marking surface 28 which approximates the curvature of the corneoscleral junction.

A second protuberance 30 adjoins one end of the first protuberance, while a third protuberance 34 adjoins the opposite end of the first protuberance. Each of the second and third protuberances includes an edge defining a second marking surface 32 and a third marking surface 36, respectively. The second and third protuberances and their associated marking surfaces extend substantially parallel to each other and are in opposing relation along a first axis extending through them.

A fourth protuberance 38 is positioned in opposing relation to a central portion of the first protuberance along a second axis running substantially perpendicular to the first axis which extends through the second and third protuberances. It includes an edge defining a fourth marking surface 40. The front surface of protuberance 38 corresponds to the front surface 22. All of the edges of the protuberances are sharp enough to leave distinct depressions when pressed against the surface of the eye, but are not so sharp as to cause incisions to be made in eye tissue. The marking surfaces are positioned to allow them to simultaneously engage the surface of the eye. As the surface of the eye is curved, they are not required to be coplanar as shown. The desired depressions or other markings of the cornea can accordingly be made by simply pressing the head thereagainst.

An alignment line 42 extends across at least one of the superior or front surfaces of the block, and preferably both of these surfaces. The alignment line may be in the form of a ridge or a depression, and is preferably different in color from the surfaces of the block to enhance its visibility. It can alternatively be a line which is printed or painted on the block surfaces. The alignment line substantially bisects the block. As the protuberances are substantially centered with respect to the inferior surface of the block, a plane extending through the alignment line will bisect the first and fourth protuberances and extend midway between and parallel to the second and third protuberances. The alignment line, the symmetrical arrangement of the protuberances and the correspondence between the first arcuate marking surface 28 and the corneoscleral junction allow the surgeon to precisely mark the surface of the eye.

The corneal marker in accordance with the preferred embodiment of the invention is designed to assist the surgeon in making an incision of selected length and width. In view of the desire to maintain a maximum incision width to length ratio of about 3:2 when performing clear corneal surgery, the marking surfaces are positioned such that the surgeon can safely stay within this ratio. Specifically, the ratio of the distance between the second and third marking surfaces 32, 36 and the distance between the first and fourth marking surfaces 28, 40 is about 3:2. Commercially available phacoemulsion probes require incision widths of 2.0 to 3.5 mm, the distance between the second and third marking surfaces preferably fall within this range. This range may expand as future phacoemulsification probes evolve. The distance between the first and fourth marking surfaces is therefore preferably between 1.33 and 2.33 mm.

Figure 1:
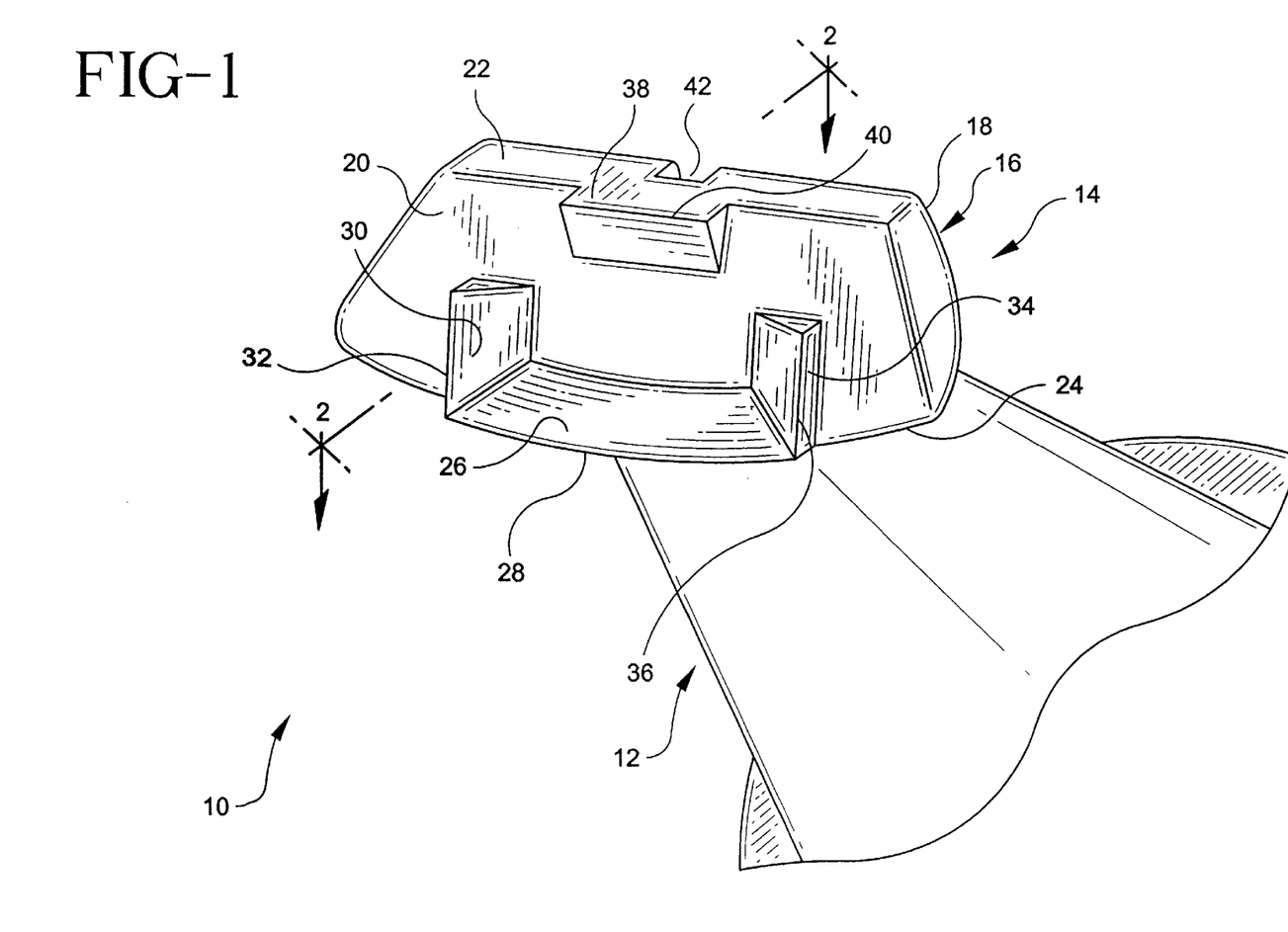
FIG. 1 is a perspective view showing a corneal marker according to the invention.
Figure 2:
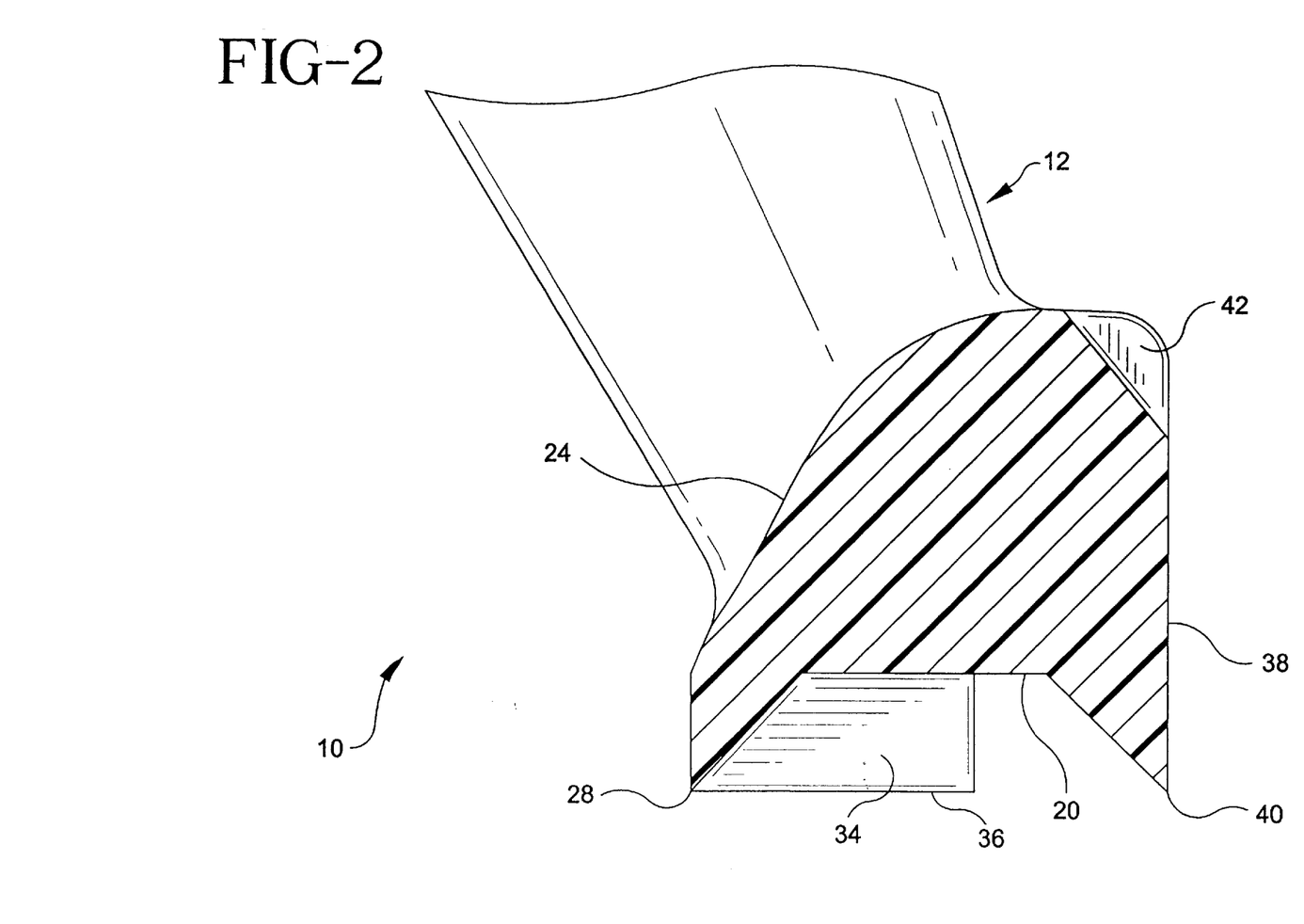
FIG. 2 is a sectional elevation view taken from section 2—2 of FIG. 1.
Figure 3:
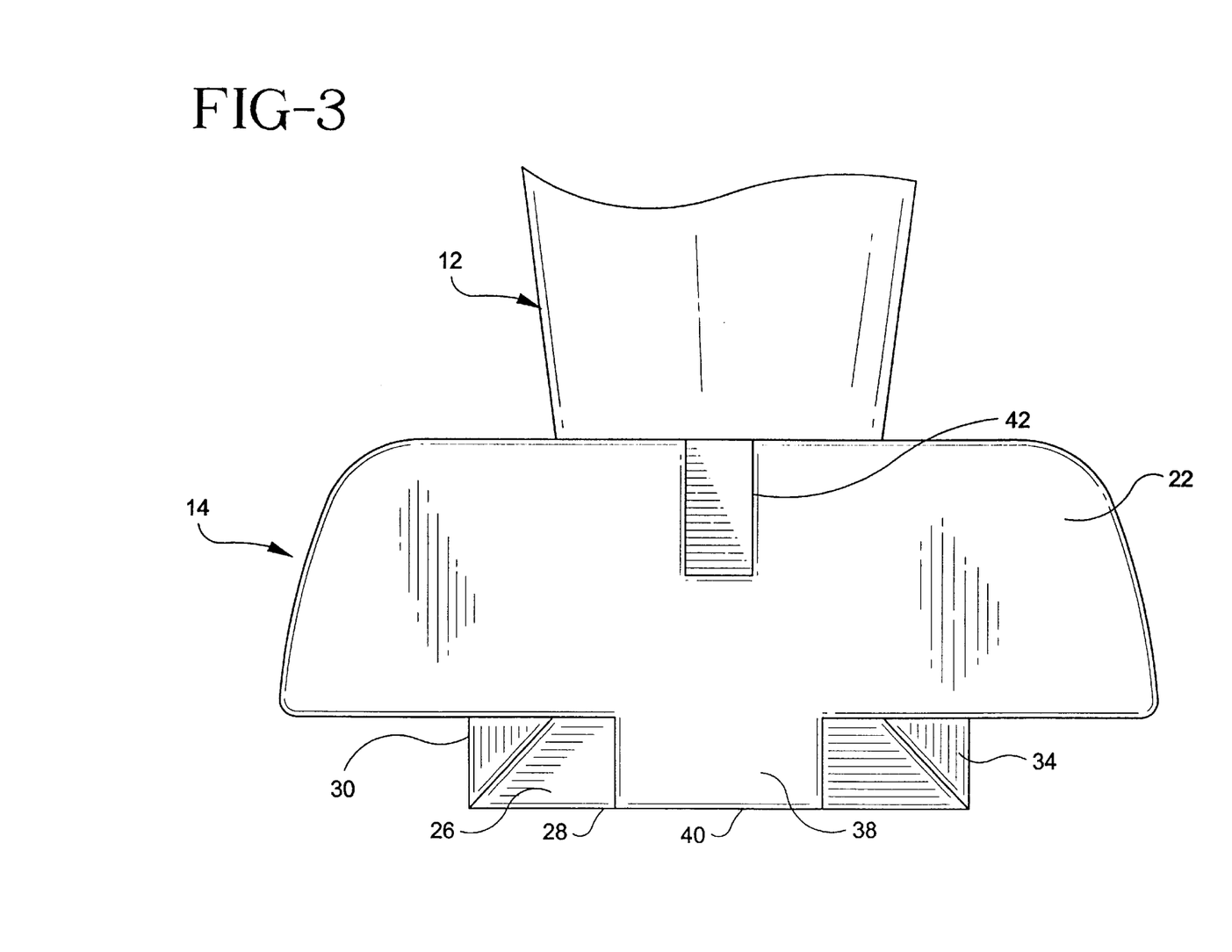
FIG. 3 is a front elevation view thereof.
Figure 4:
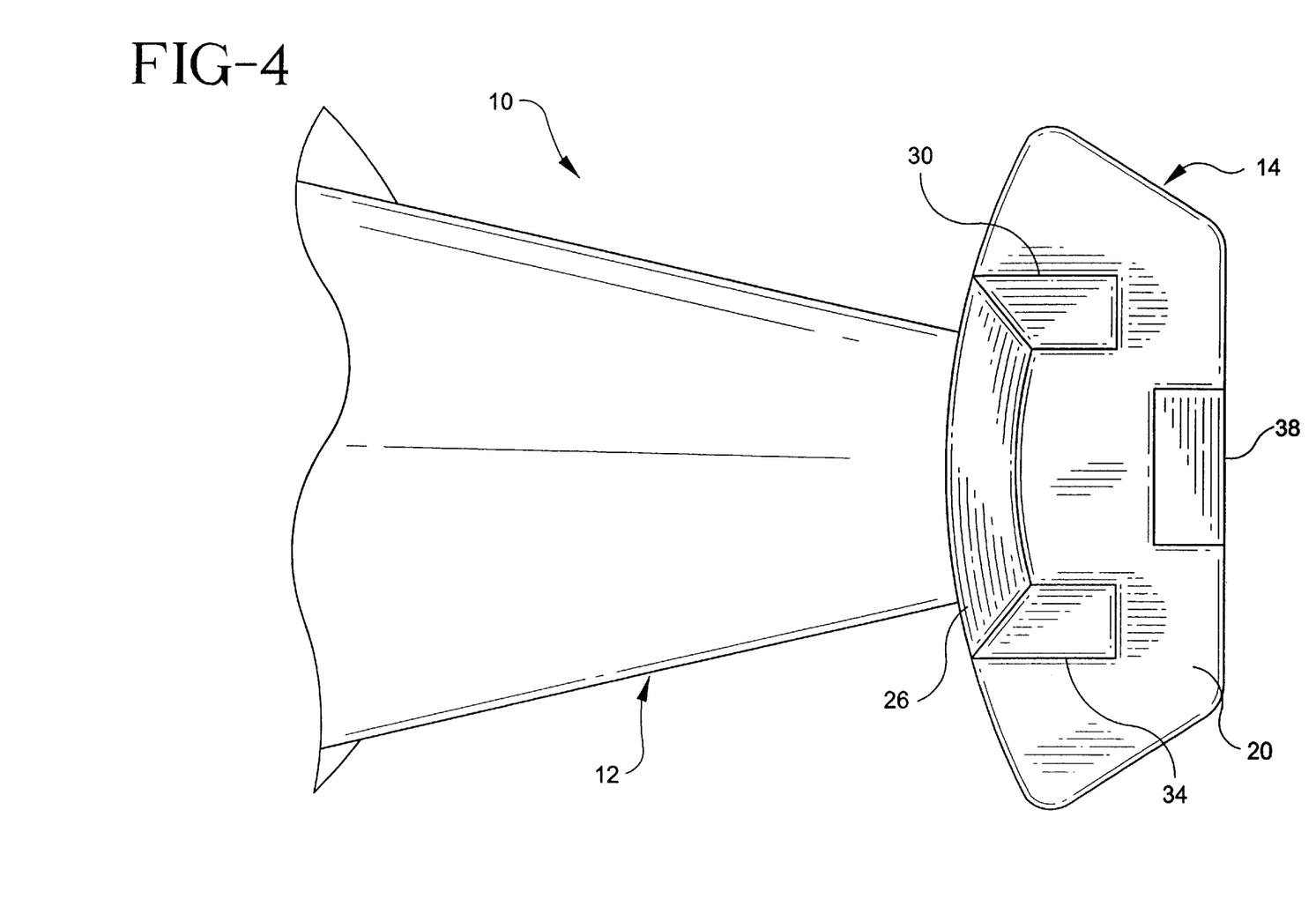
FIG. 4 is a bottom plan view thereof.
Figure 5:
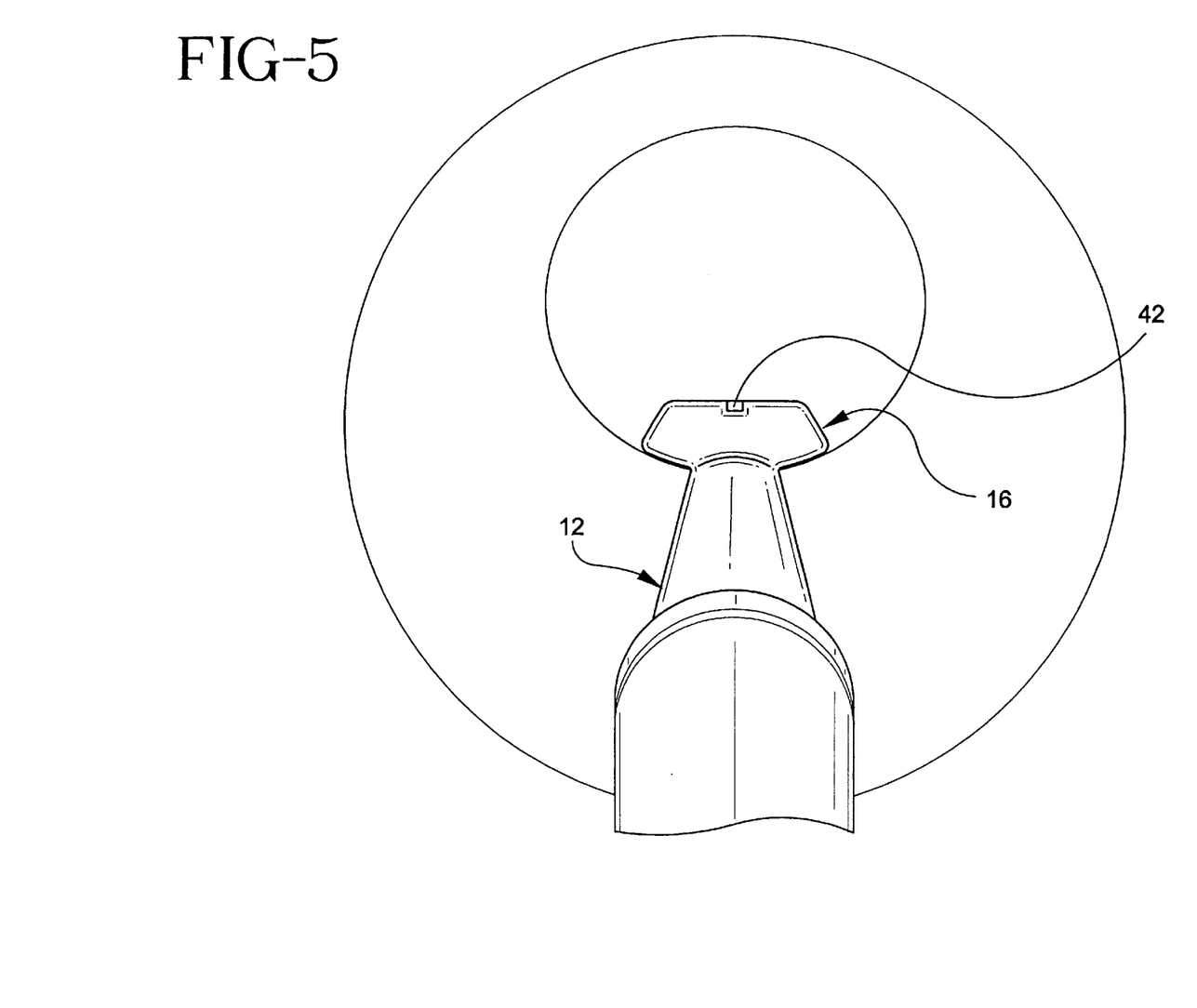
FIG. 5 is a top view showing use of the corneal marker in marking the corneal tissue of the the eye.
Figure 6:
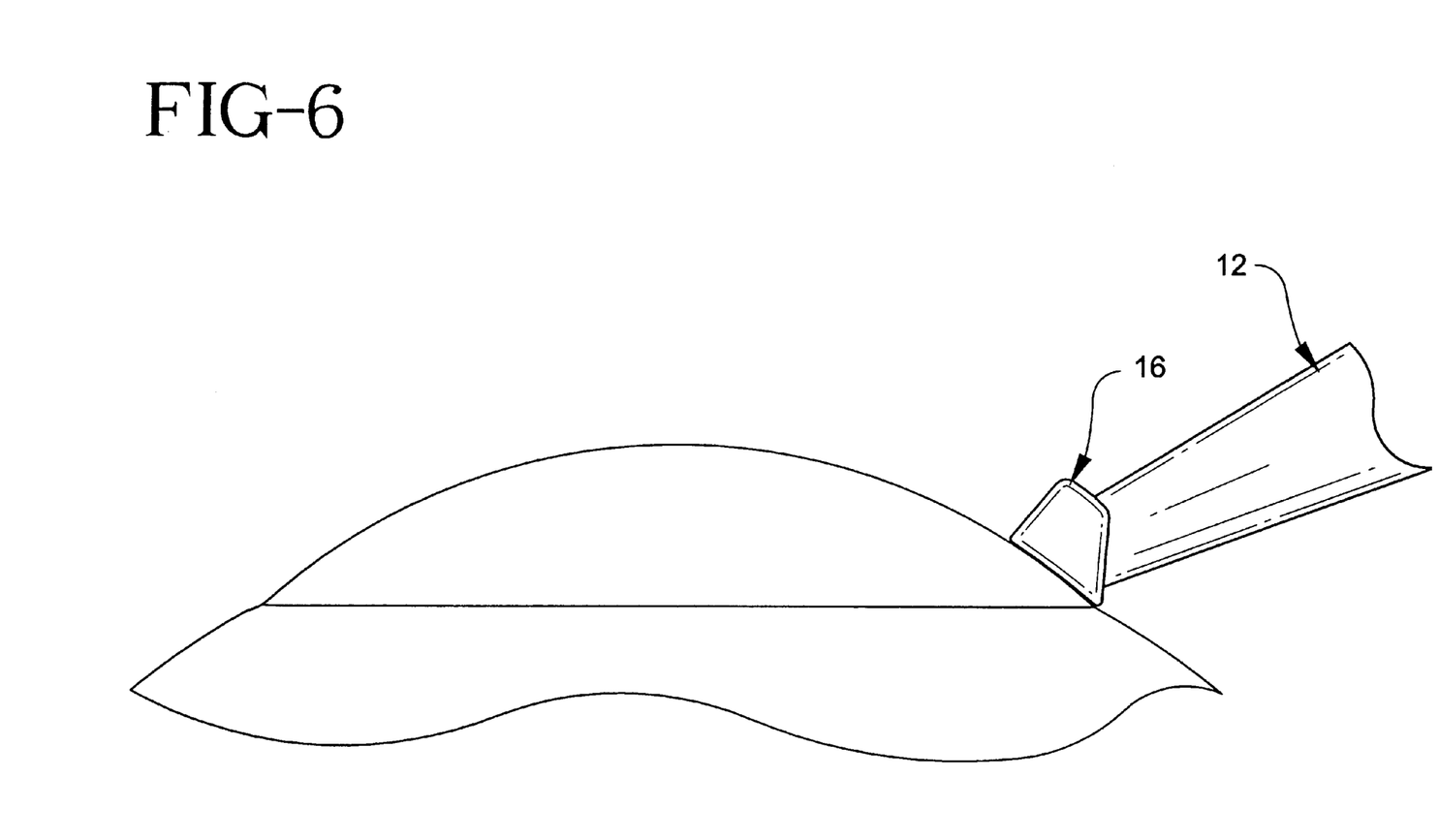
FIG. 6 is a side elevation view thereof.
Figure 7:
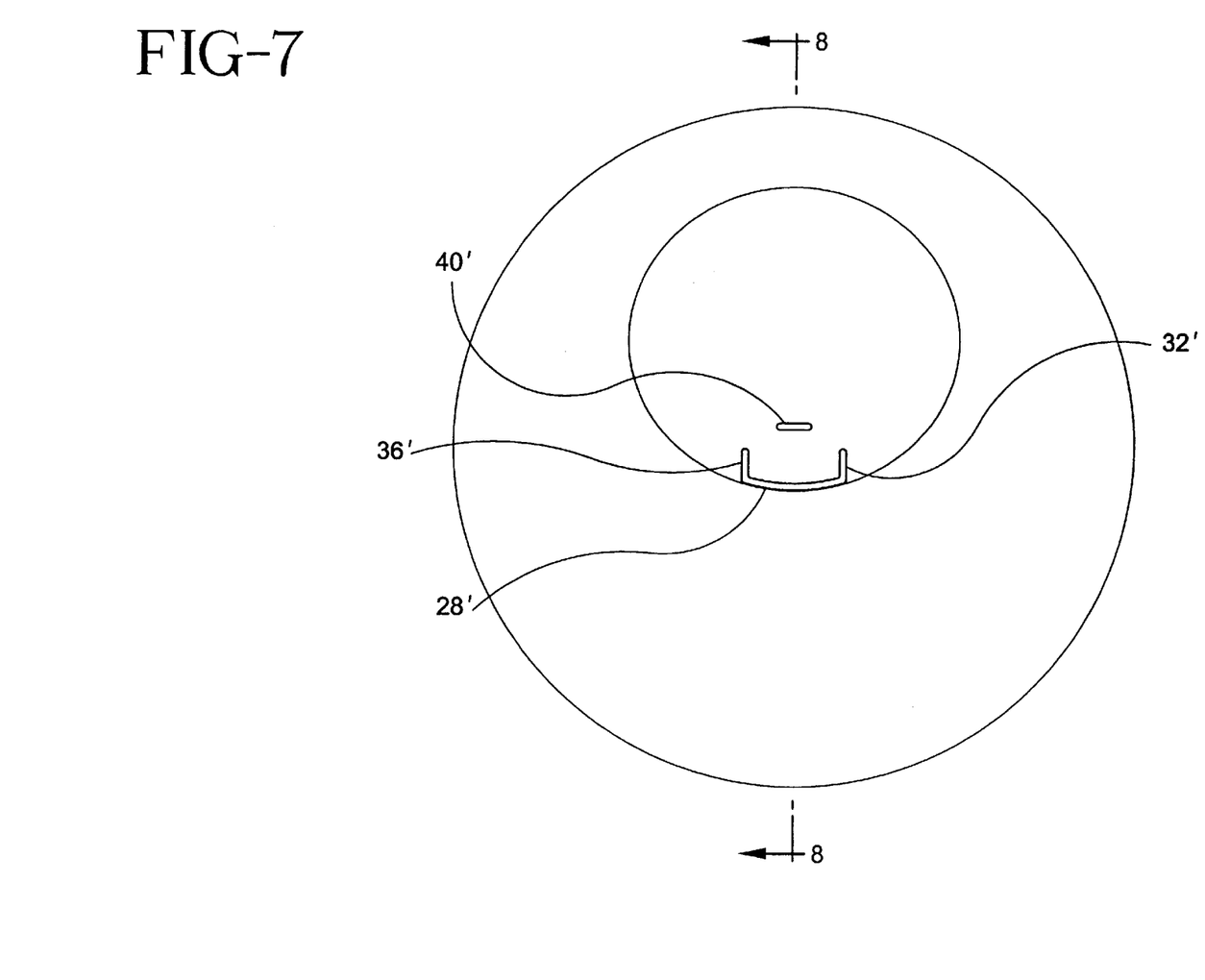
FIG. 7 is a top view of schematically illustrated eye including markings created by the corneal marker.
Figure 8:
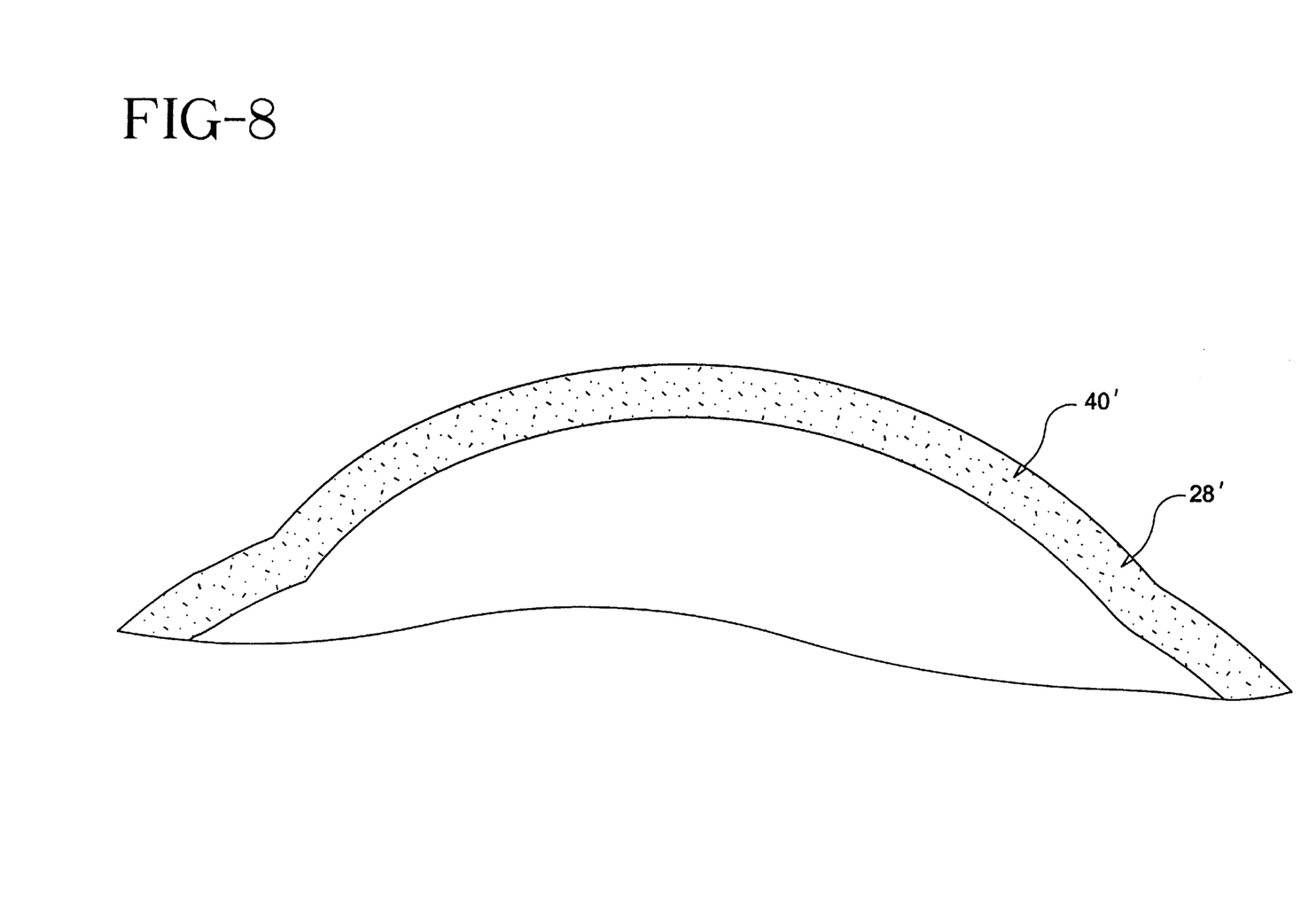
FIG. 8 is a sectional view thereof, taken from section 8—8 of FIG. 7.

The corneal marker as described above functions as a template to guide a surgeon as incisions are made in eye tissue. Prior to surgery, the inferior side of the block of the corneal marker is positioned such that the alignment line 42 on the superior and/or front surfaces of the block is aligned with the meridian where the primary incision is to be made. The edge 28 of the marker is simultaneously aligned with the latitude where the initial groove and/or the keratome blade will be initially inserted. This latitude is often in close proximity to the corneoscleral junction when cataract surgery is to be performed. Once the location of the marker has been set, the surgeon presses the inferior surface of the block against the eye, leaving markings on the cornea. FIGS. 5 and 6 schematically illustrate the step of positioning the corneal marker 10, while FIG. 7 schematically illustrates the markings which are provided on the cornea and/or adjoining tissue following use of the marker. The markings correspond to the configuration of the marking surfaces 28, 32, 36 and 40, and form a generally rectangular outline. It will be appreciated that an acceptable rectangular outline can be formed through the use of marking surfaces formed from either continuous or discontinuous edges. The fourth marking surface need not be linear as its only intended function is to indicate the length of the tunnel formed beneath the surface of the cornea.

The markings 28', 32', 36' and 40' left by the marker may be in the form of depressions in the eye tissue and/or lines of ink. A sterile ink may accordingly be applied to the marking surfaces, 28, 32, 36 and 40 of the marker prior to its engagement with the cornea if desired.

Figure 9:
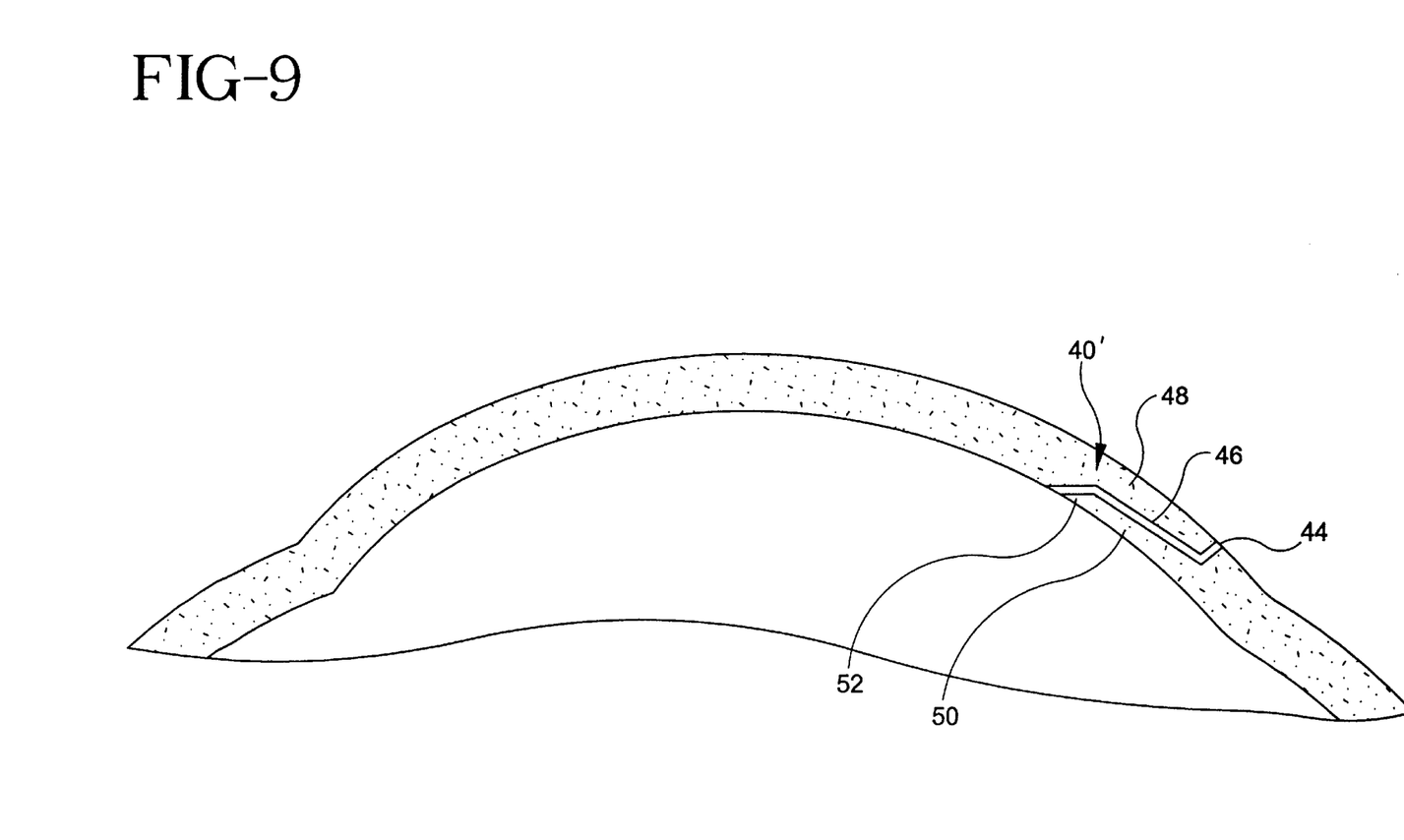
FIG. 9 is a sectional view taken from section 8—8 showing a clear corneal incision.

In operations where a corneal groove is to be created, the incision can be initiated at one of the two markings 32',36' and extended along mark 28' to the other such marking. The corneal groove is typically about 0.3 to about 0.6 mm in depth perpendicular to the tissue, and is made in corneal or limbal tissue. A corneal groove 44 is shown schematically in FIG. 9. Following the formation of the groove, the surgeon may engage the tip of a keratome or crescent knife at the base of the groove centered between the two radial marks 32', 36' on mark 28'. The knife is angled such that the plane of the cutting edge is substantially parallel to the corneal surface. The tissue is then dissected towards the mark 40', keeping the blade within the confines of marks 32' and 36' maintaining the parallel relationship between the knife blade and the corneal surface and thereby forming the tunnel. As shown in FIG. 9, the tunnel 46 is bounded by a roof 48 and a base 50. When the blade tip coincides with the mark 40', the surgeon using the keratome knife angles the knife handle forwardly, causing the blade to applanate the cornea. The blade is then moved forwardly towards the interior of the eye, entering the anterior chamber. A flap 52 is thereby formed at the distal end of the tunnel, as shown in FIG. 9. Following surgery, the flap is maintained against the tunnel roof by intraocular pressure, thereby preventing leakage. The incision created using the above procedure has a maximum width to length ratio of about three to two.

As discussed above, the width of the primary incision is determined by the size of the phacoemulsion probe used to fragment the cataractous lens. As probe sizes presently vary between about 2.0 and about 3.5 mm, a number of blade width sizes are available for making incisions of the appropriate sizes. A corresponding number of corneal markers would be available to surgeons for use with such blades. Alternatively, a single corneal marker could include multiple sets of marking surfaces providing rectangular outlines of selected sizes so that the marker could be used in conjunction with blades of different widths. The use of a dedicated marker for each blade width is preferred.

The marker is designed such that it can be manufactured using metal casting, metal injection molding, machining, or plastic injection molding. While the particular material(s) from which it is made is not deemed critical, it is necessary that the marker be sterile when used by the surgeon. The ability of the marking surfaces to hold ink is necessary in the event the surgeon desires to mark the cornea with ink rather than indentations alone. The disclosed corneal marker is designed and dimensioned for use in cataract surgery through the use of a clear corneal incision. Other surgical procedures could possibly be facilitated through the use of the marker where controlling the length and width of an incision are deemed important.

REFERENCES

1. Fine, I. H. Architecture and construction of a self-sealing incision for cataract surgery. J. Cataract Refract Surg 1991; 17:672–676.

2. Mackool, R. J., Russell, R. S. Strength of clear corneal incisions in cadaver eyes. J. Cataract Refract Surg 1996; 22:721–725.

What is claimed is:

1. A corneal marker comprising:
    a handle,
    a head coupled to said handle, said head including first, second, third and fourth marking surfaces positioned for engagement of a human cornea, said first marking surface including an elongated edge portion and being in opposed relation to said fourth marking surface along a first axis, said second and third marking surfaces including elongated edge portions and being in opposed relation to each other along a second axis running generally perpendicular to said axis, said marking surfaces defining a generally rectangular outline wherein the width of said outline is about one and one-half times the length of said outline, the width of said outline being defined by the distance between said second and third marking surfaces and the length of said outline defined by the distance between said first and fourth marking surfaces; and said head further comprising a block having an inferior surface and a superior surface, and a plurality of protuberances extending from said inferior surface, said protuberances respectively including said marking surfaces.

2. The corneal marker as described in claim 1, wherein the distance between said second and third marking surfaces is between about 2.0 and about 3.5 mm.

3. The corneal marker as described in claim 2, wherein said first marking surface is arcuate.

4. The corneal marker as described in claim 3, wherein said first marking surface includes end portions respectively adjoining said second and third marking surfaces.

5. The corneal marker as described in claim 4, wherein said fourth marking surface includes an elongated edge portion opposing a central portion of said first marking surface.

6. A corneal marker comprising:
    a handle,
    a head coupled to said handle, said head including first, second, third and fourth marking surfaces positioned for engagement for a human cornea, said first marking surface being arcuate and including an elongated edge portion, said first marking surface in opposed relation to said fourth marking surface along a first axis,
    said second and third marking surfaces including elongated edge portions and being in opposed relation to each other along a second axis running generally perpendicular to said first axis wherein the distance between said second and third marking surfaces is between about 2.0 mm and about 3.5 mm,
    said marking surfaces generally defining a rectangular outline, the width of said outline is about one and one-half times the length of said outline, when the width of said outline is defined by the distance between said second and third marking surfaces and the length of said outline defined by the said distance between said first and fourth marking surfaces, said head further comprising a block having an inferior surface and a superior surface, and a plurality of protuberances extending from said inferior surface, said protuberances respectively including said marking surfaces, and
    said block includes a front surface extending between said inferior and superior surfaces, and an alignment line formed on at least one of said superior in said front surfaces and substantially bisecting said block, said front surface of said block is straight and adjacent to the fourth marking surface.

7. The corneal marker as described in claim 6, wherein said block includes an arcuate rear surface, one of said protuberances adjoining said rear surface and defining said first marking surface.

8. The corneal marker as described in claim 7, wherein said first marking surface includes end portions respectively adjoining said second and third marking surfaces.

9. The corneal marker as described in claim 8, wherein said fourth marking surface includes an elongated edge portion opposing a central portion of said first marking surface.

10. A corneal marketing comprising:

a handle;

a head coupled to said handle, said head including a superior surface, an inferior surface, a front surface, and a rear surface, said rear surface being arcuate;

first, second, third and fourth protuberances extending from said inferior surface of said head, said protuberances including edge portions defining first, second, third and fourth marking surfaces, respectively;

said first protuberance adjoining said rear surface of said head and including an arcuate edge portion defining said first marking surface;

said fourth protuberance adjacent to said front surface and being in opposing relation to a central portion of said first protuberance along a first axis;

said second and third protuberances being in opposing relation to each other along a second axis running perpendicular to said first axis, the distance between said second and third marking surfaces being between about 2.0 mm and about 3.5 mm, said head further comprises a block having an inferior surface and a superior surface, in a plurality of protuberances extending from said inferior surface, said protuberances respectively including said marking surfaces, and wherein the distance between said second and third marking surfaces is about one and one-half times said first and fourth marking surfaces.

11. The corneal marker as described in claim 10, wherein said second and third marking surfaces are elongated and substantially parallel to each other.

12. The corneal marker as described in claim 10, including an alignment line extending along said superior and front surfaces of said head.

13. The corneal marker as described in claim 10, wherein the distance between said second and third marking surfaces is about fifty percent greater than the distance between said first and fourth marking surfaces.

14. The corneal marker as described in claim 10, wherein said front surface of such head is straight.

15. A method of making an incision in eye tissue of selected length and width, comprising:

marking the surface of an eye to provide first, second, third and fourth markings thereon such that said first and fourth markings are in opposing relation along a first axis and said second and third markings are in opposing relation along a second axis running substantially perpendicular to said first axis, the distance between said second and third markings is not more than about fifty percent greater than the distance between said first and fourth markings, and at least said second, third and fourth markings are made on corneal tissue;

forming an initial groove at said first marking substantially perpendicularly into said eye tissue;

causing a surgical knife having a tip to form a tunnel running substantially parallel to the surface of said cornea beginning at said groove and until the tip of said knife coincides with said fourth marking, and applanating the cornea when the tip of said knife coincides with said fourth marking.

16. A method as described in claim 15 including the step of causing said first marking to be arcuate in form and positioned near the corneoscleral junction.

17. A method as described in claim 15 including the step of causing said initial groove and said tunnel to have a width substantially equal to the distance between said second and third markings, said width being between about 2.0 and about 3.5 mm, and moving said knife into the anterior chamber following applanation of the cornea.

18. A corneal marker comprising:

a handle;

a head coupled to said handle, said head including a superior surface, an inferior surface, a front surface, and a rear surface, said rear surface being arcuate;

first, second, third and fourth protuberances extending from said inferior surface of said head, said protuberances including edge portions defining first, second, third and fourth marking surfaces, respectively;

said first protuberance adjoining said rear surface of said head and including an arcuate edge portion defining said first marking surface;

said fourth protuberance adjacent to said front surface and being in opposing relation to a central portion of said first protuberance along a first axis;

said second and third protuberances being in opposing relation to each other along a second axis running perpendicular to said first axis, the distance between said second and third marking surfaces being between about 2.0 mm and about 3.5 mm;

said head further comprises a block having an inferior surface and a superior surface, in a plurality of protuberances extending from said inferior surface, said protuberances respectively including said marking surfaces, said front surface of said head corresponding with said fourth marking surface for increased visibility of the cornea; and wherein the distance between said second and third marking surfaces is about one and one-half times said first and fourth marking surfaces being less than the distance between said second and third marking surfaces.

* * * * *